(12) United States Patent
Matsuguma et al.

(10) Patent No.: US 9,551,646 B2
(45) Date of Patent: Jan. 24, 2017

(54) APPARATUS FOR ENVIRONMENTAL TEST

(71) Applicant: ESPEC CORP., Osaka-shi, Osaka (JP)

(72) Inventors: Osamu Matsuguma, Osaka (JP);
Tetsuya Shimada, Kobe (JP); Shuichi Kanazawa, Ayabe (JP)

(73) Assignee: ESPEC CORP., Osaka (JP)

( * ) Notice: Subject to any disclaimer, the term of this patent is extended or adjusted under 35 U.S.C. 154(b) by 404 days.

(21) Appl. No.: 14/230,417

(22) Filed: Mar. 31, 2014

(65) Prior Publication Data

US 2015/0090053 A1 Apr. 2, 2015

(30) Foreign Application Priority Data

Sep. 30, 2013 (JP) ................................ 2013-203524

(51) Int. Cl.
*G01N 17/00* (2006.01)
(52) U.S. Cl.
CPC .................... *G01N 17/002* (2013.01)
(58) Field of Classification Search
None
See application file for complete search history.

(56) References Cited

U.S. PATENT DOCUMENTS

| | | | | |
|---|---|---|---|---|
| 5,008,082 A | * | 4/1991 | Shaw | 422/65 |
| 5,851,143 A | | 12/1998 | Hamid | |
| 5,876,666 A | * | 3/1999 | Lin et al. | 422/29 |
| 8,231,846 B2 | * | 7/2012 | Hughes | 422/554 |
| 2009/0249823 A1 | | 10/2009 | Okuda et al. | |
| 2010/0167334 A1 | * | 7/2010 | Williamson, IV | 435/29 |
| 2012/0108461 A1 | * | 5/2012 | Bussan et al. | 506/9 |
| 2013/0053724 A1 | * | 2/2013 | Fiebig et al. | 600/567 |

FOREIGN PATENT DOCUMENTS

| | | |
|---|---|---|
| CN | 1264019 A | 8/2008 |
| CN | 203437138 U | 2/2014 |
| JP | 2-101251 | 8/1990 |
| JP | 11-270959 | 10/1999 |
| JP | 2000-146821 | 5/2000 |
| JP | 2000171387 | 6/2000 |
| JP | D1158594 | 11/2002 |
| JP | 2007-303791 | 11/2007 |
| JP | 2008-014546 | 1/2008 |
| KR | 300510210 | 10/2008 |
| KR | 954129 | * 4/2010 |

OTHER PUBLICATIONS

Office Action Dated Dec. 28, 2015.

* cited by examiner

*Primary Examiner* — Robert R Raevis
(74) *Attorney, Agent, or Firm* — Gerald E. Hespos; Michael J. Porco; Matthew T. Hespos

(57) ABSTRACT

An apparatus for environmental tests includes a chamber having formed therein a test space for disposing a sample, and a tray that is provided on the upper surface of the chamber and has an open upper surface. A front wall of the tray is configured by an operation unit where switches are provided. A rear wall of the tray is configured by a control unit housing a control substrate. A left wall and a right wall of the tray are configured by hollow bodies connecting the operation unit and the control unit. The tray is covered with a lid.

10 Claims, 20 Drawing Sheets

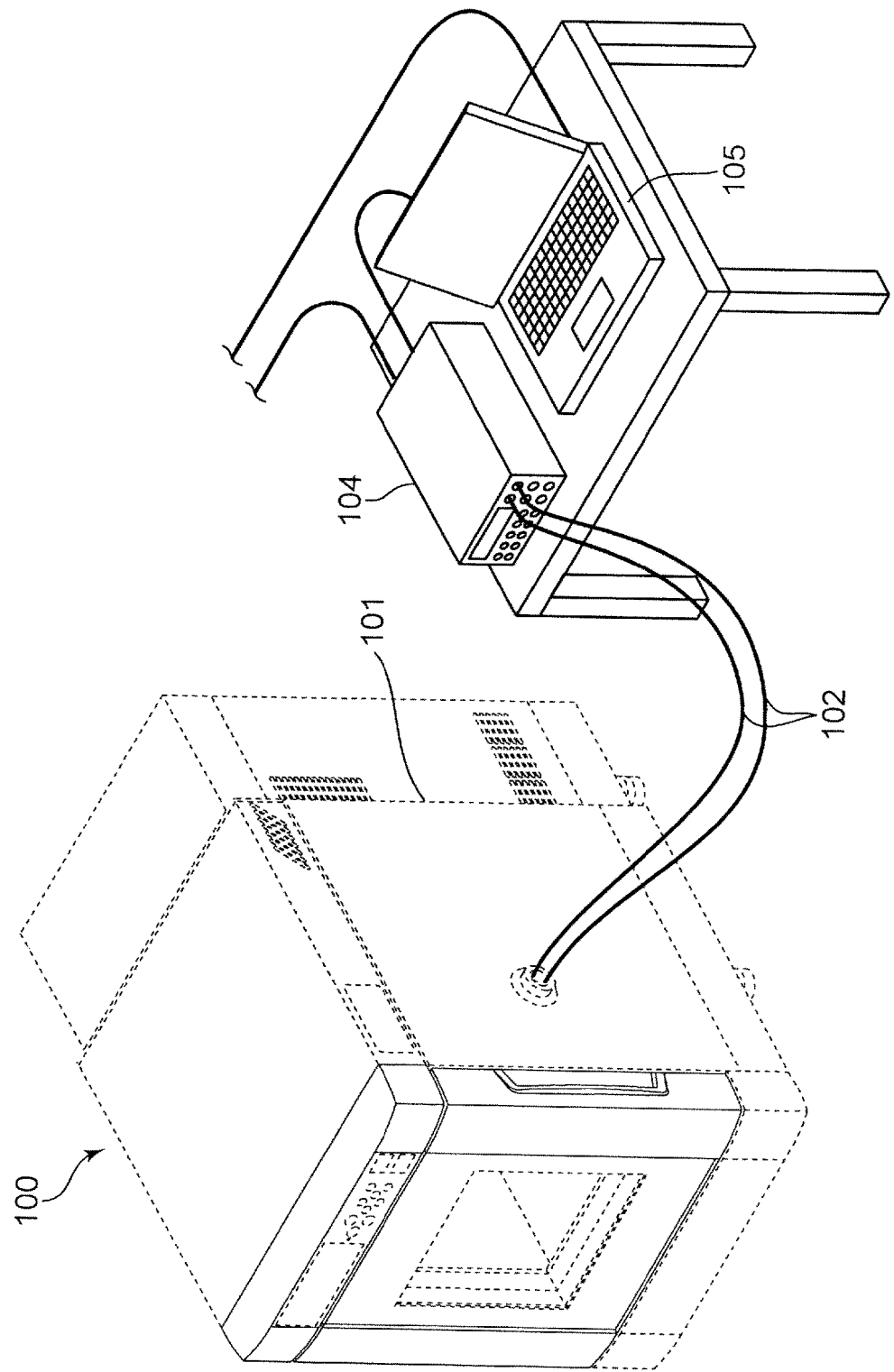

APPARATUS FOR ENVIRONMENTAL TEST

BACKGROUND

1. Technical Field

The present invention relates to an apparatus for environmental tests.

2. Description of Related Art

An apparatus for environmental tests is known in which a sample is accommodated in a chamber and exposed to a predetermined temperature-humidity environment to test the sample for performance, quality and reliability such as service life, as disclosed in Japan Design Registration Publication No. 1158594. When environmental testing of a sample such as a printed board is performed, there is a case where, for example, a wiring 102 connected to the sample accommodated in a chamber 101 is connected to a measuring instrument 104, as shown in FIG. 23, and a computer 105 is used for processing the measurement data obtained with the measuring instrument 104. In this case, the measuring instrument 104 and the computer 105 are disposed close to an apparatus for environmental tests 100.

Where the measuring instrument 104 and the computer 105 are used, a large number of wirings such as signal wires or power supply wires are present around the apparatus for environmental tests 100. In addition, materials relating to the test, tools, and a large number of other objects also can be present around the apparatus for environmental tests. Therefore, the environment surrounding the apparatus for environmental tests 100 is degraded and those wirings can hinder the environmental testing operations.

SUMMARY

It is an object of the present invention to provide an apparatus for environmental tests in which the degradation of the environment surrounding the apparatus for environmental tests can be inhibited.

According to one aspect of the present invention, an apparatus for environmental tests includes a chamber having formed therein a test space for disposing a sample, and a tray that is provided on an upper surface of the chamber and has an open upper surface.

BRIEF DESCRIPTION OF THE DRAWINGS

FIG. 23 shows a conventional apparatus for environmental tests.

DETAILED DESCRIPTION OF THE PREFERRED EMBODIMENTS OF THE INVENTION

A mode for carrying out the present invention is described hereinbelow in detail with reference to the appended drawings.

The apparatus for environmental tests according to the present embodiment is configured as a temperature and humidity chamber in which a sample is exposed to an atmosphere under predetermined temperature conditions and humidity conditions, and a thermal load is applied to the sample. The apparatus for environmental tests may be also configured as a temperature chamber in which a sample is exposed to a predetermined temperature atmosphere, and a thermal load is applied to the sample.

Figure 1:
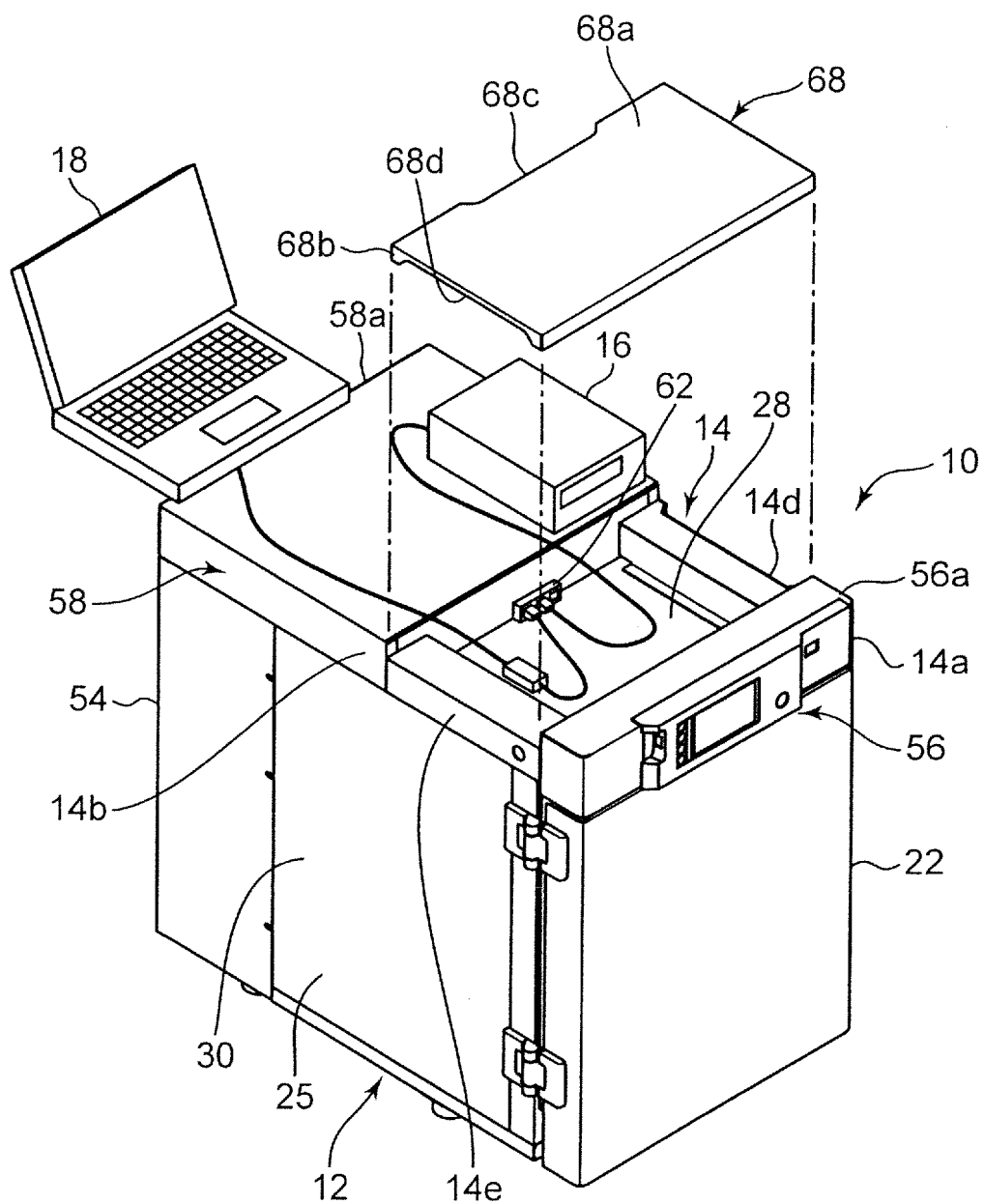
FIG. 1 shows the external appearance of the apparatus for environmental tests according to the embodiment of the present invention.

As shown in FIG. 1, the apparatus for environmental tests 10 of the present embodiment includes a chamber 12 and a tray 14 provided on the upper surface of the chamber 12. When a test is performed in the apparatus for environmental tests 10, there is a case where a measuring instrument 16 and a personal computer 18 are connected to the chamber 12 or the tray 14.

Figure 2:
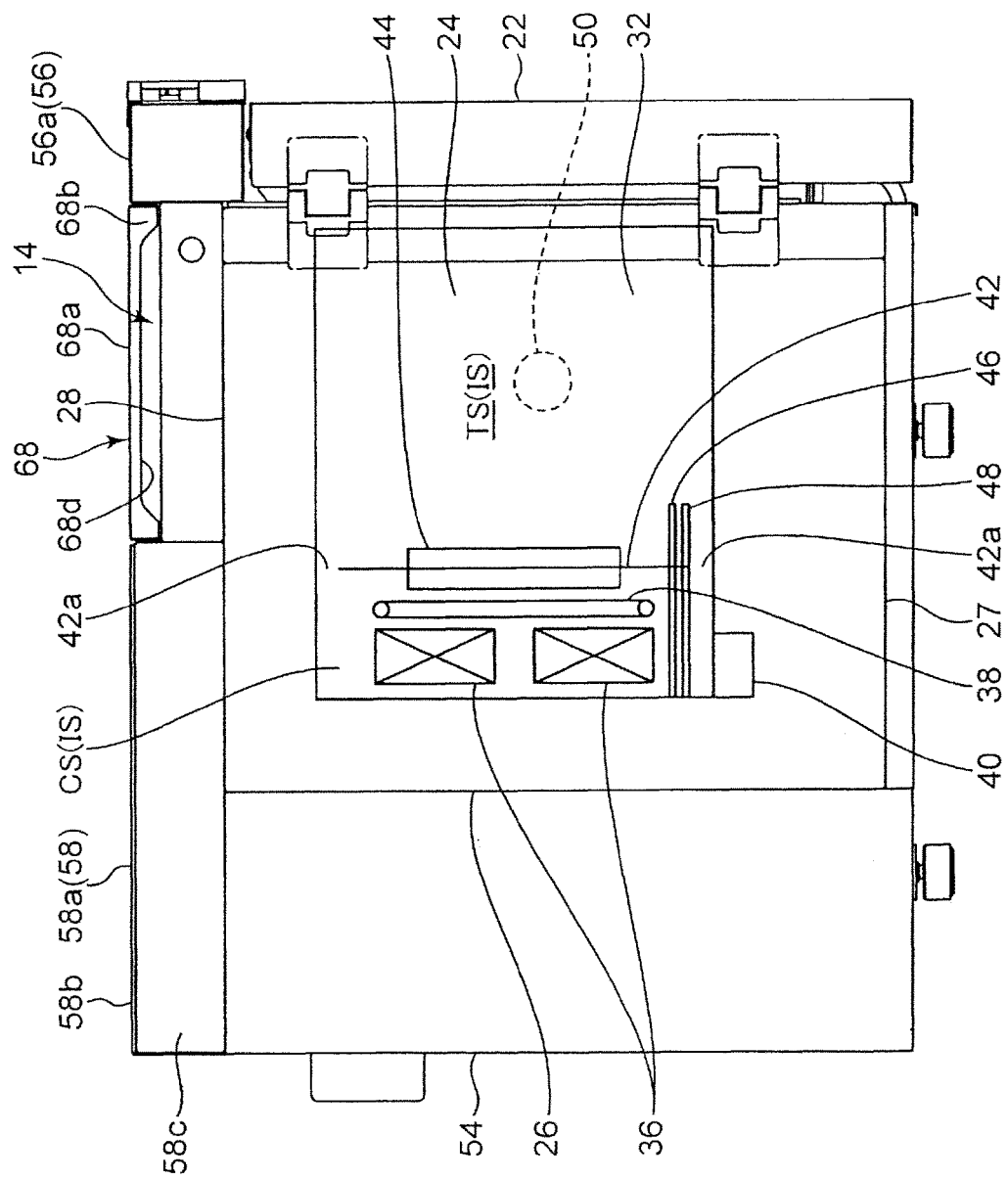
FIG. 2 illustrates the internal configuration of a chamber in a side view of the apparatus for environmental tests.

As shown in FIG. 2, the chamber 12 is provided with a door 22 constituting a front wall, a left wall 24, a right wall 25, a rear wall 26, a bottom portion 27, and a top portion 28 and is formed, as a whole, in a rectangular parallelized shape. An inner space IS bounded by the door 22, left wall (side wall on the right side when viewed from the front) 24, right wall (side wall on the left side when viewed from the front) 25, rear wall 26, bottom portion 27, and top portion 28 is formed in the chamber 12. A test space TS for disposing a sample, and a conditioning space CS that communicates with the test space TS and serves to condition the air supplied into the test space TS are included in the inner space IS. The test space TS is formed in a substantially rectangular parallelepiped shape. The conditioning space CS is not necessarily formed as part of the inner space IS inside the chamber 12 and may be formed outside the chamber 12 and configured to communicate with the test space TS formed inside the chamber 12 by a through path (not shown in the figure) passing through the chamber 12.

The door 22, left wall 24, right wall 25, rear wall 26, bottom portion 27, and top portion 28 are each constituted by an outer wall plate 30 configured by a metal plate or the like, an inner wall plate 32 (see FIG. 2) configured by a metal plate or the like and disposed at a distance from the outer wall plate 30, and a thermally insulating material (not shown in the figure) provided between those outer wall plate 30 and inner wall plate 32.

An evaporator 36 which is a cooling unit for cooling the air, a heater 38 which is a heating unit for heating the air, and a humidifier 40 which is a humidification unit for humidifying the air are disposed in the conditioning space CS. A fan 44 which is a blower that blows the air located in the conditioning space CS into the test space TS is disposed in a partitioning member 42 partitioning the conditioning space CS and the test space TS. Further, a temperature sensor (dry-bulb sensor) 46 which is a temperature sensor for detecting the air temperature in the test space TS, and a wet-bulb sensor 48 are disposed in the inner space IS. A communication hole 42a for returning the air located in the test space TS into the conditioning space CS is formed in the partitioning member 42. Therefore, inside the inner space IS, the air circulates between the conditioning space CS and the test space TS.

A communication hole 50 for connecting the test space TS with the outside of the chamber 12 is formed in the left wall 24 of the chamber 12 (see FIG. 2). A wiring connected to the sample can be drawn out to the outside through the communication hole 50. The communication hole 50 can be closed with a cover (not shown in the figure).

A machine room 54 is provided at the rear-surface side (back-surface side) of the chamber 12. A refrigerator (not shown in the figure) for circulating a heat medium through the evaporator 36 is disposed in the machine room 54.

An operation unit 56 and a control unit 58 are disposed on the chamber 12. The operation unit 56 and the control unit 58 are disposed in the order of description from the front side. The operation unit 56 is positioned directly above the door 22 (see FIG. 2) and, therefore, disposed in front of the top portion 28.

Figure 3:
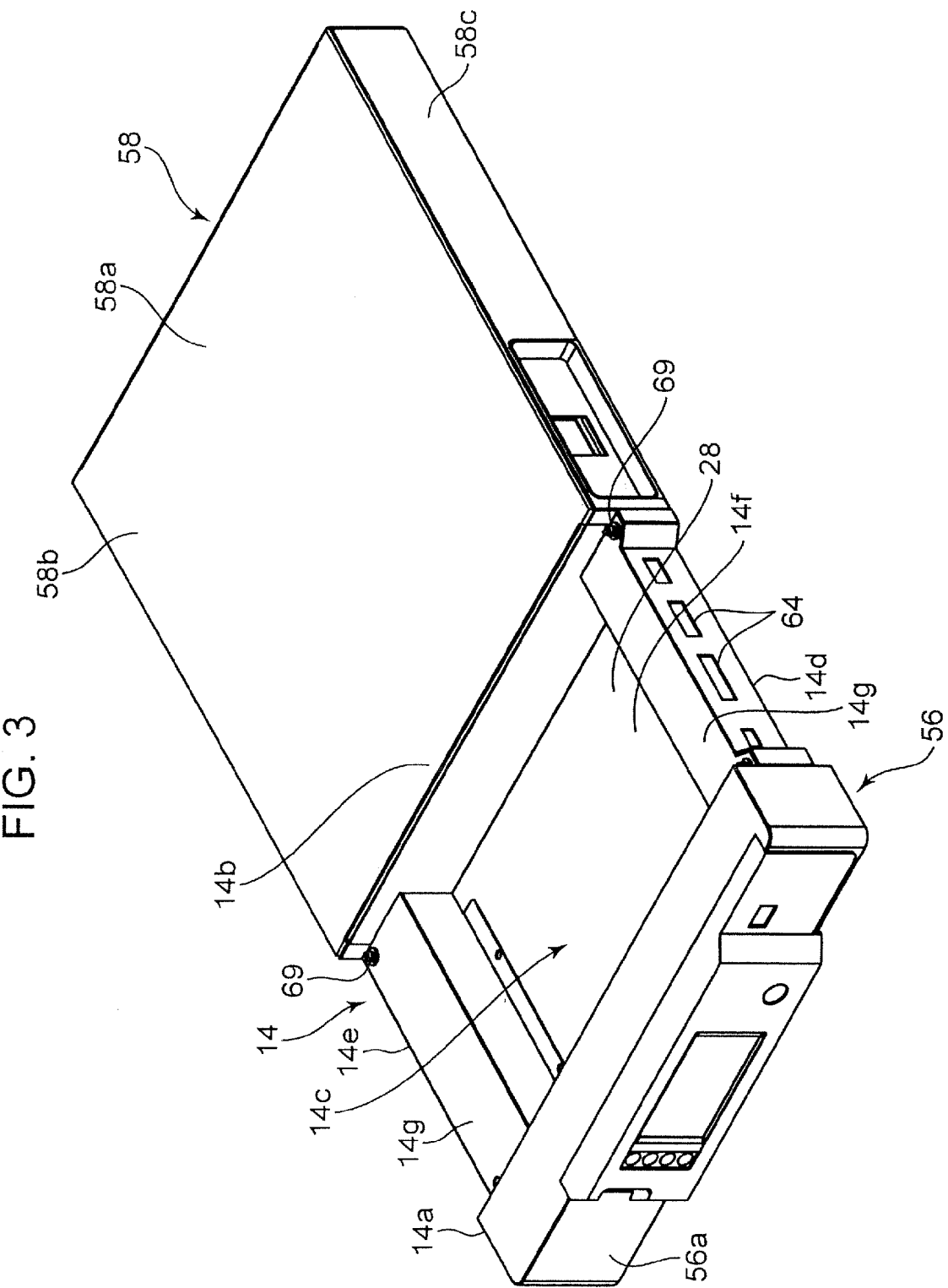
FIG. 3 shows the operation unit, tray and control unit of the apparatus for environmental tests.

The operation unit 56 has a configuration in which a control substrate (not shown in the figure) is housed inside a case 56a. The case 56a is mainly formed from a metal plate, and plastic parts are used therein. As shown in FIG. 3, the operation unit 56 is formed in an external shape extending in the left-right direction. Operation switches, a display unit functioning as an input-output unit and the like are provided on the front surface of the operation unit 56. The case 56a of the operation unit 56 has a predetermined height and a width substantially equal to the width (length in the left-right direction) of the chamber 12 (see FIG. 1). The height of the case 56a of the operation unit 56 is the same along the entire width direction.

The control unit 58 has a configuration in which a control substrate and electronic devices (not shown in the figure) are housed inside a case 58a. The case 58a of the control unit 58 is constituted by a metal plate, has an upper surface disposed flush with the upper surface of the operation unit 56, and is formed as a whole in a flat rectangular parallelepiped shape (see FIGS. 2 and 3). The control unit 58 is provided in a range from the chamber 12 to the machine room 54 and disposed above the chamber 12 and the machine room 54.

The operation unit 56 and the control unit 58 are disposed at a predetermined distance from each other, the operation unit 56 also functions as a front wall 14a of the tray 14, and the control unit 58 also functions as a rear wall 14b of the tray 14. In other words, the front wall 14a of the tray 14 is constituted by the operation unit 56, and the rear wall 14b of the tray 14 is constituted by the control unit 58. The gap between the operation unit 56 and the control unit 58 functions as an accommodation portion 14c which is the depression of the tray 14. The accommodation portion 14c of the tray 14 is partitioned by the case 56a from the interior of the operation unit 56 and also partitioned by the case 58a from the interior of the control unit 58. Therefore, a screw, a wiring or the like accommodated in the accommodation portion 14c is prevented from penetrating into the operation unit 56 or control unit 58. Therefore, safety is ensured.

Figure 4:
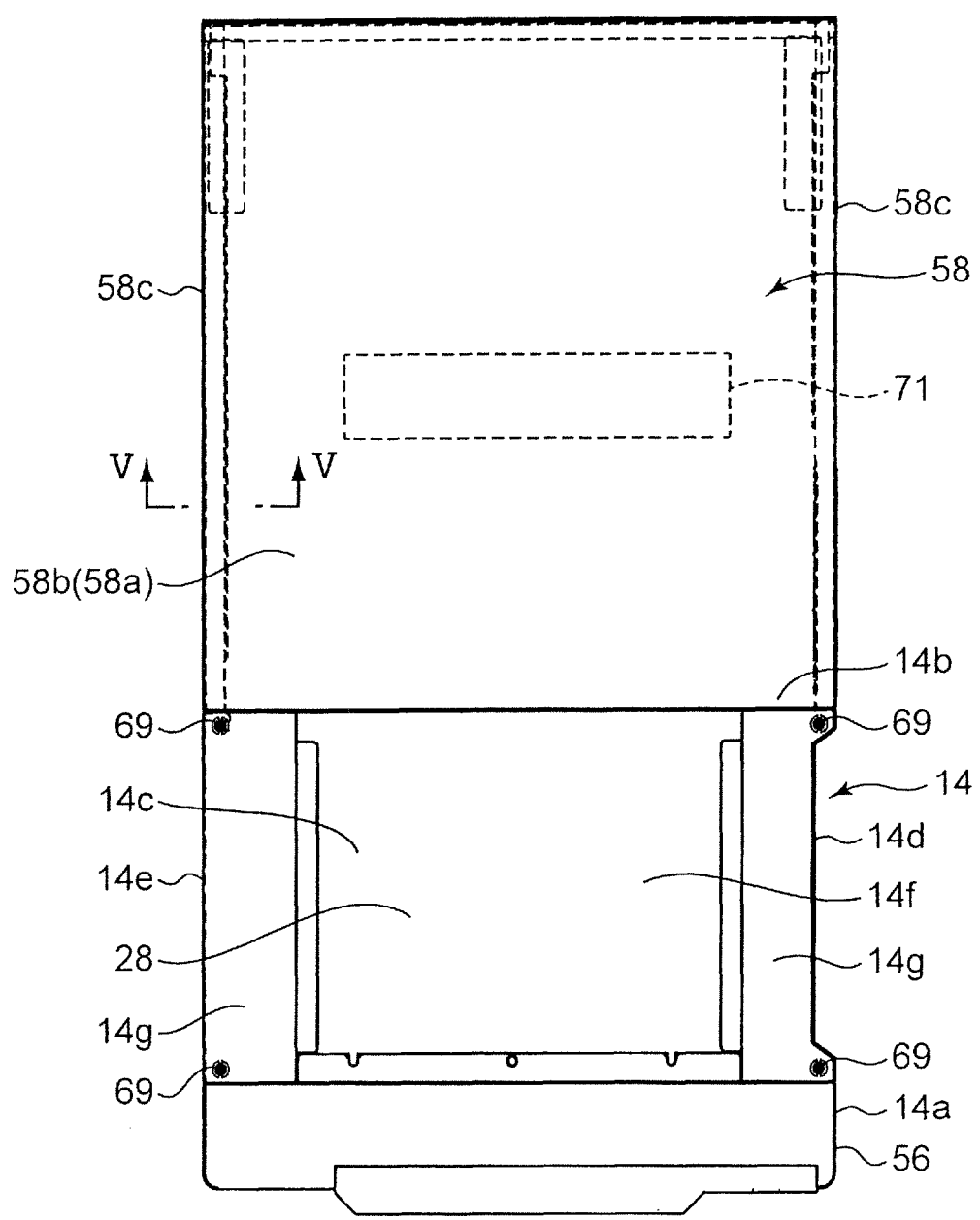
FIG. 4 shows the configuration inside the control unit in a top view of the operation unit, tray, and control unit.

As shown in FIGS. 3 and 4, the tray 14 has the front wall (operation unit 56) 14a, the rear wall (control unit 58) 14b, a left wall 14d which is a side wall on the left side (side wall on the right side when viewed from the front), and a right wall 14e which is a side wall on the right side (side wall on the left side when viewed from the front). The top portion 28 of the chamber 12 constitutes a bottom portion 14f of the tray 14. Articles such as wirings, materials relating to the test, and tools can be accommodated in the accommodation portion 14c of the tray 14.

A connector 62 may be provided inside the tray 14, as shown in FIG. 1, on the front surface of the control unit 58. The connector 62 is electrically connected to the control substrate and the like of the control unit 58. Therefore, where a signal wire connected to the measuring instrument 16 or personal computer 18 is connected to the connector 62, the control unit 58 and the measuring instrument 16 or the like are connected such as to be capable of exchanging signals.

Figure 6:
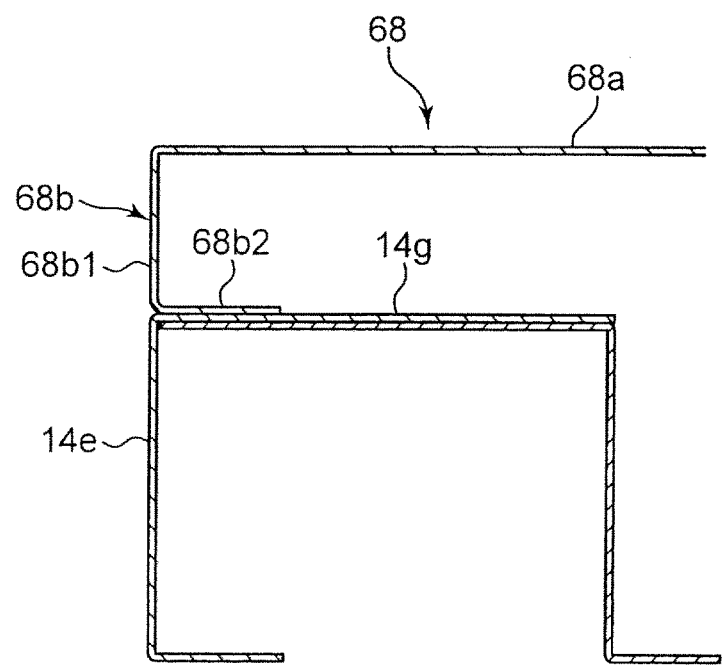
FIG. 6 is a cross-sectional view showing partially the lid and the right wall of the tray in the vicinity of the pin support portion.
Figure 7:
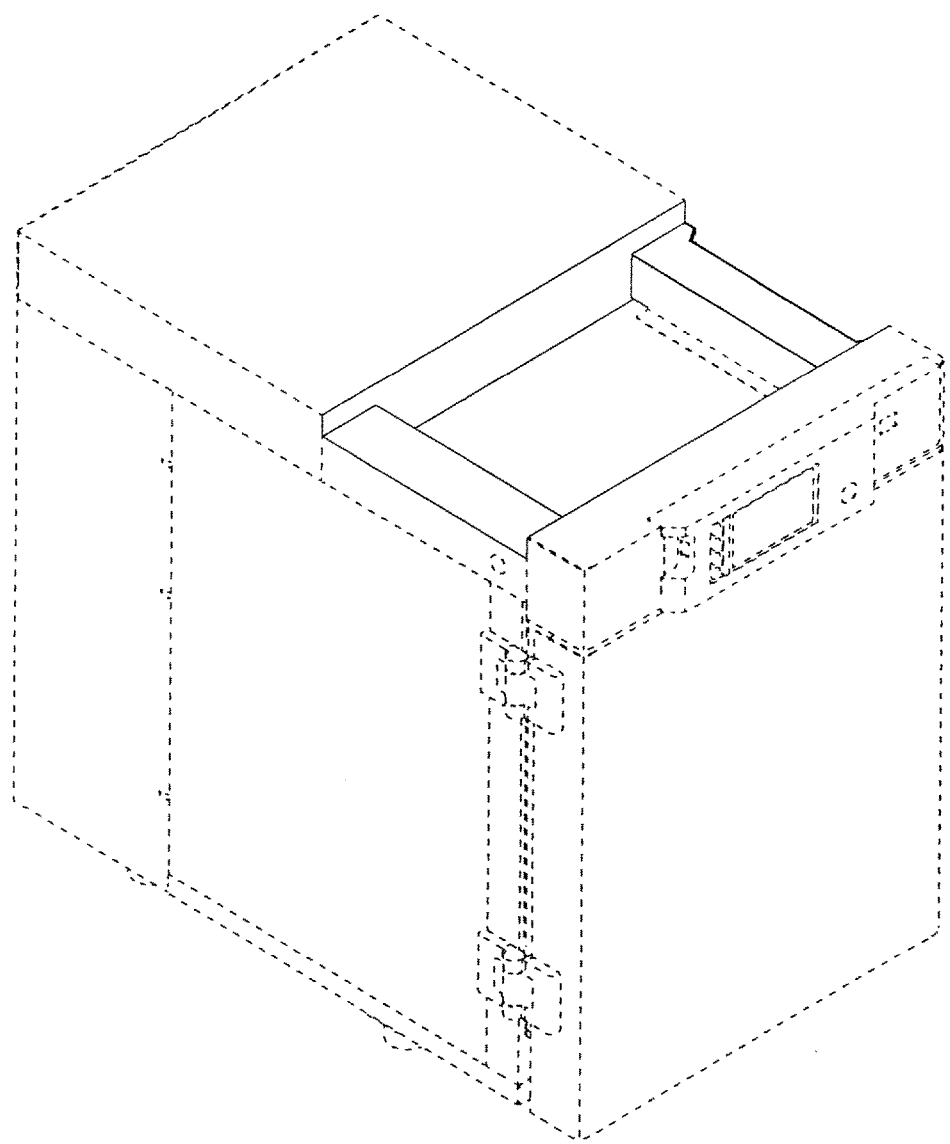
FIG. 7 is a perspective view of the temperature and humidity chamber as the apparatus for environmental tests, this view being taken from the front-surface side.
Figure 8:
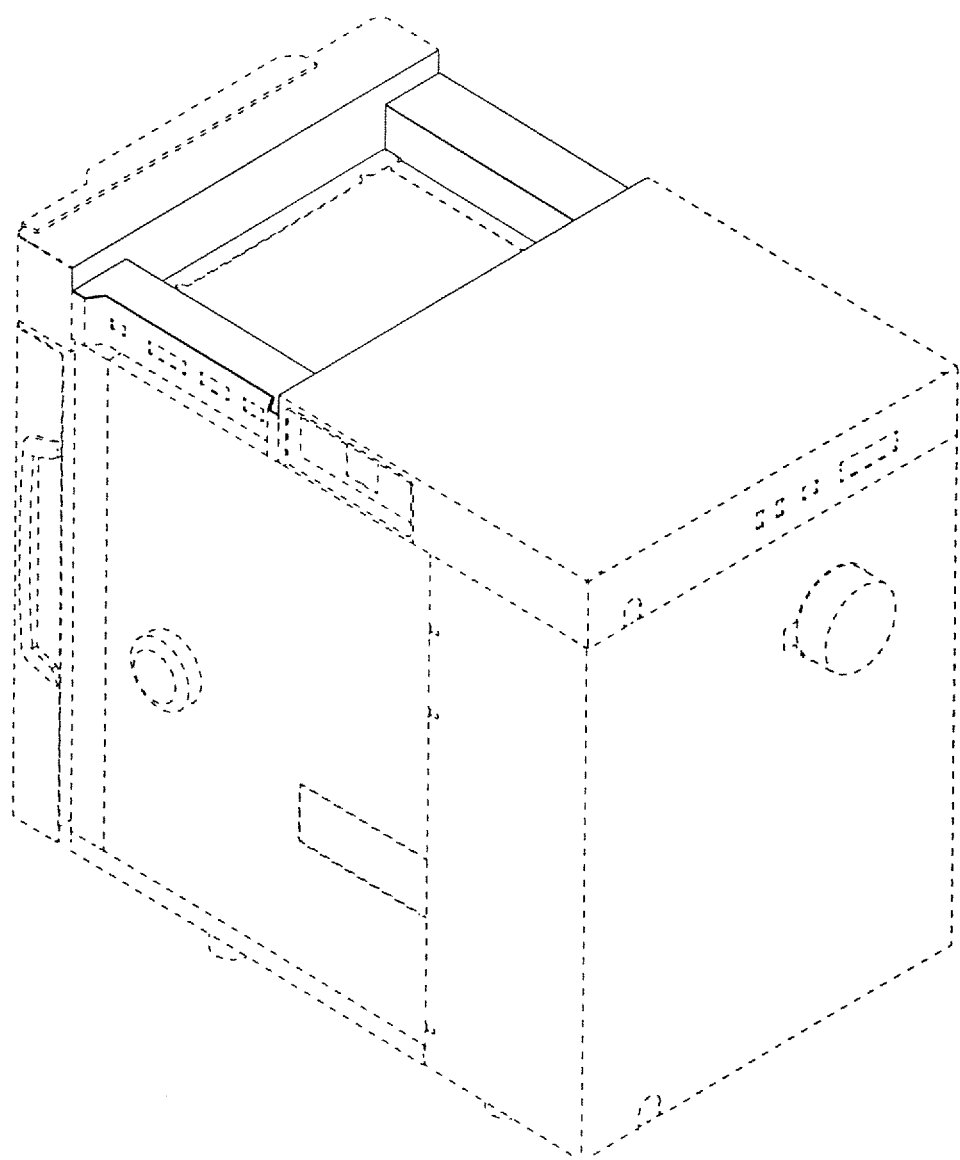
FIG. 8 is a perspective view of the temperature and humidity chamber taken from the back-surface side.
Figure 9:
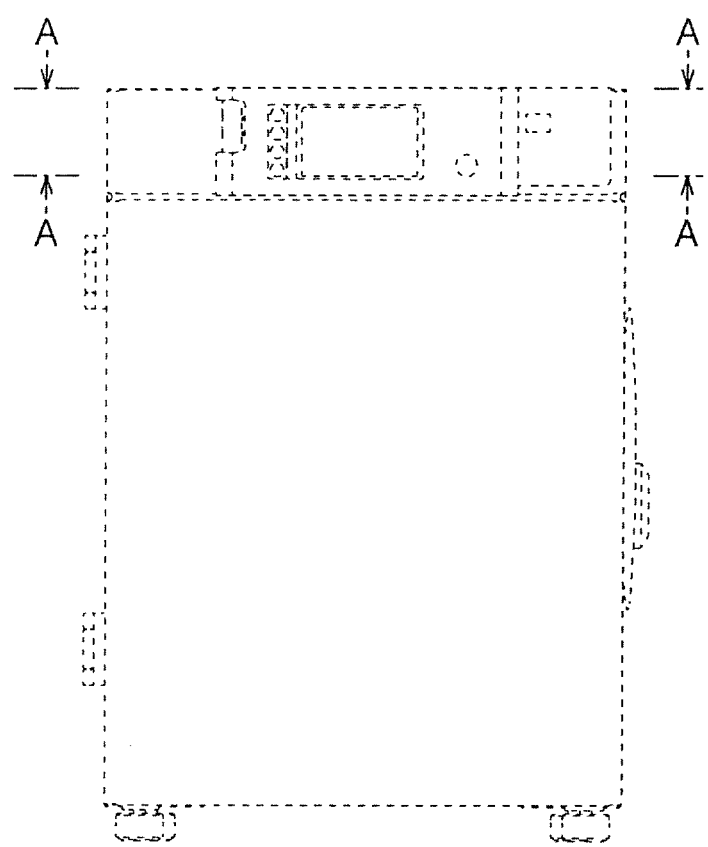
FIG. 9 is a front view of the temperature and humidity chamber.
Figure 10:
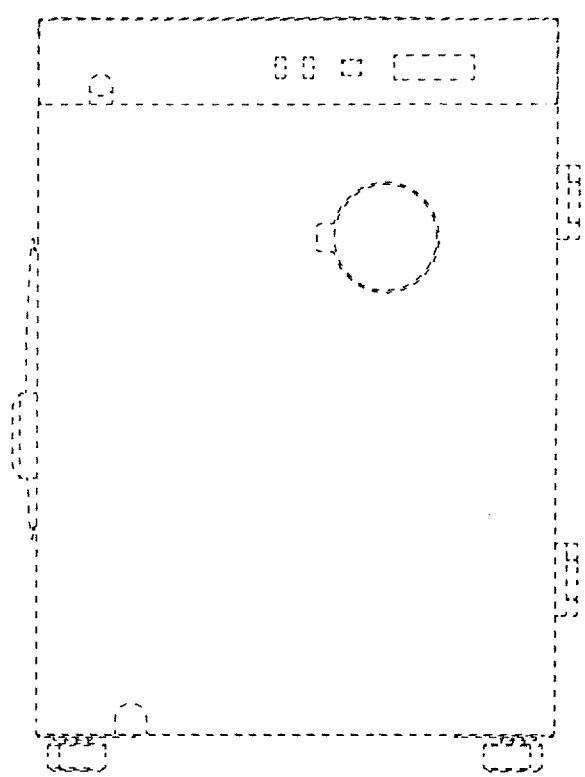
FIG. 10 is a back-surface view of the temperature and humidity chamber.
Figure 11:
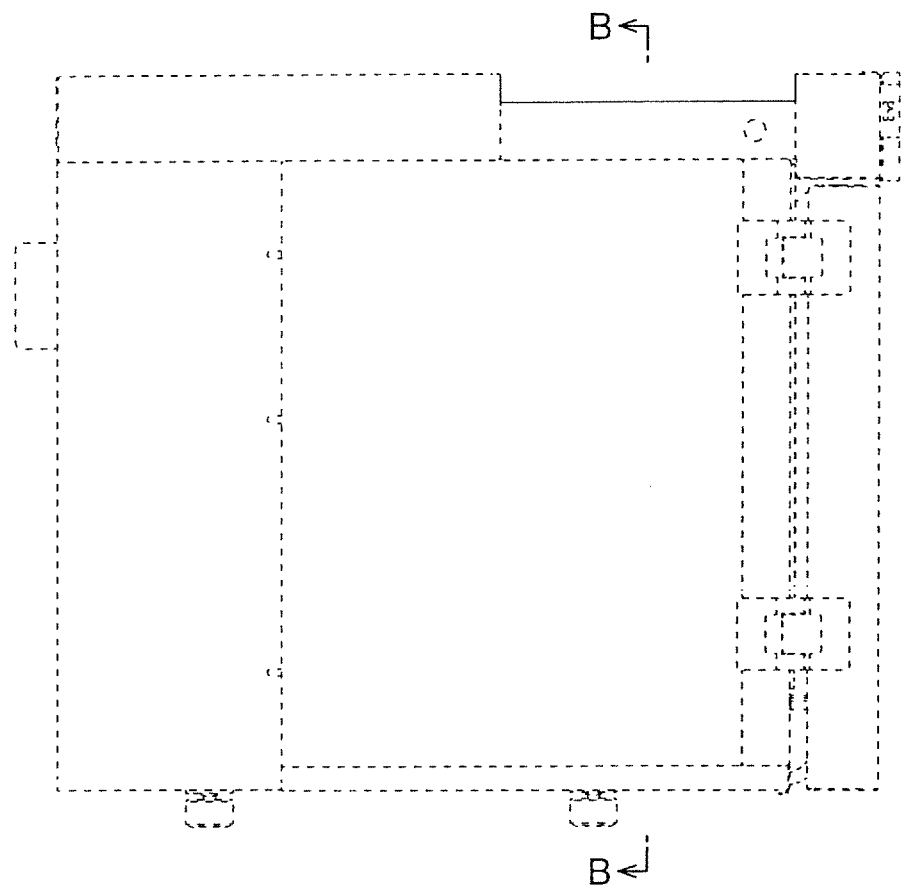
FIG. 11 is a left-side view of the temperature and humidity chamber.
Figure 12:
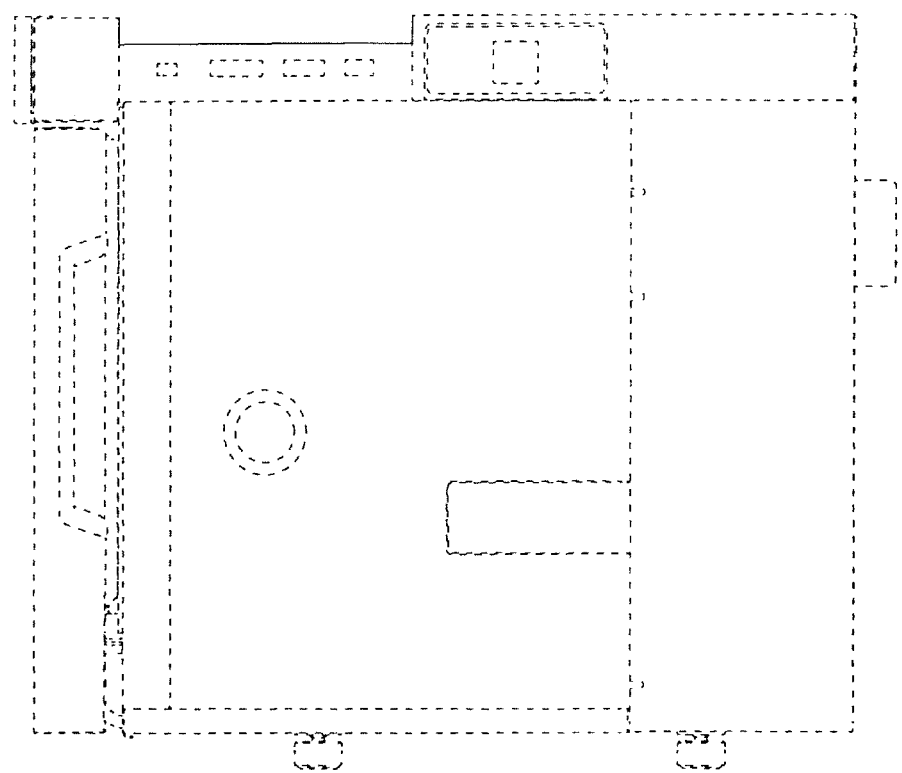
FIG. 12 is a right-side view of the temperature and humidity chamber.
Figure 13:
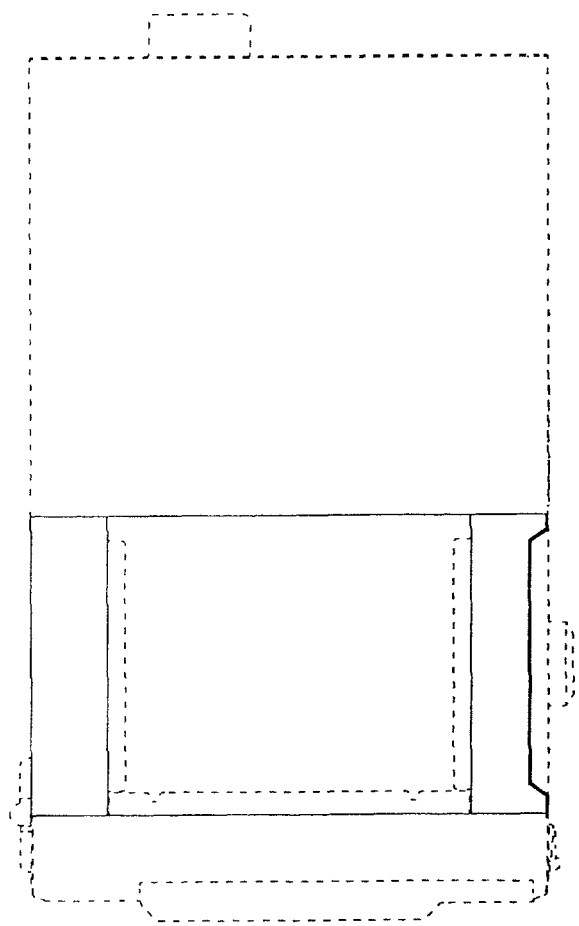
FIG. 13 is a plan view of the temperature and humidity chamber.
Figure 14:
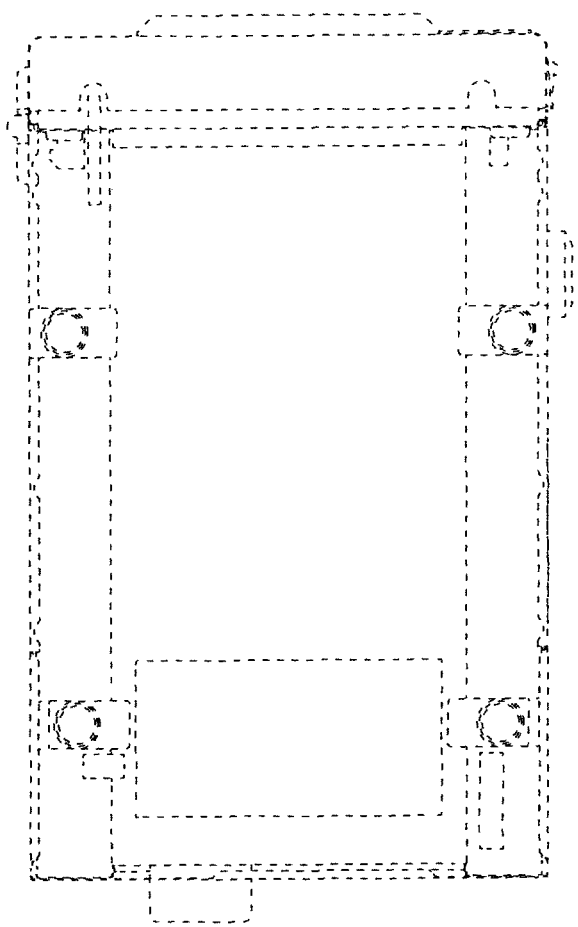
FIG. 14 is a bottom-surface view of the temperature and humidity chamber.
Figure 15:
FIG. 15 is an enlarged end-surface view of the portion A shown in FIG. 9 in which the internal structure is omitted, this view being taken along the B-B line shown in FIG. 11.
Figure 16:
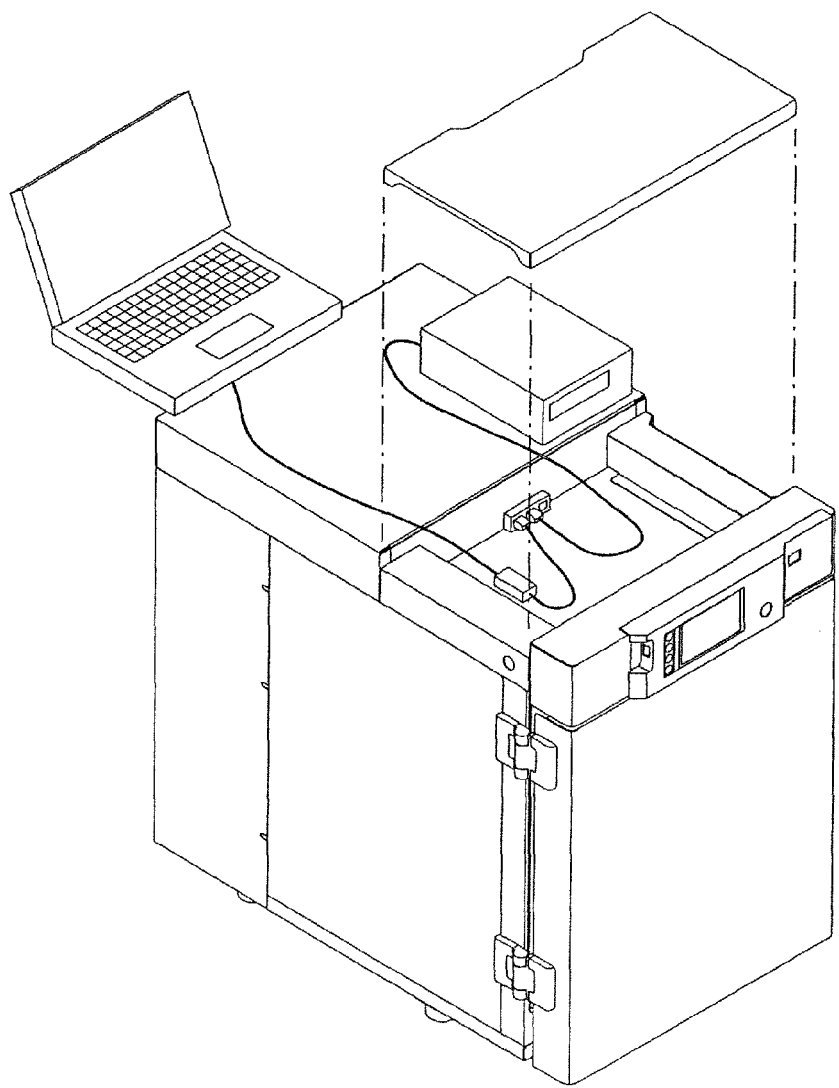
FIG. 16 shows the usage state of the temperature and humidity chamber.

The left wall 14d and the right wall 14e of the tray 14 are configured by hollow bodies connecting the operation unit 56 and the control unit 58. More specifically, the left wall 14d and the right wall 14e of the tray 14 have an angular tube configuration formed from a sheet metal (see FIG. 6 showing the right wall 14e) and are disposed on the top portion 28 of the chamber 12 such as to extend in the front-rear direction of the chamber 12. Further, the front ends of the left wall 14d and right wall 14e are connected to the rear surface of the case 56a of the operation unit 56, and the rear ends of the left wall 14d and the right wall 14e are connected to the front surface of the case 58a of the control unit 58. Therefore, the wiring connecting the control substrate provided inside the case 58a of the control unit 58 and the devices provided inside the case 56a of the operation unit 56 can pass through the space inside the side walls (left wall 14d and right wall 14e).

The right wall 14e and the left wall 14d are formed to the same height, and the height thereof is set lower than that of the operation unit 56 and the control unit 58. As a result, when a lid 68 described below is placed, the upper surface of the lid 68, the upper surface of the operation unit 56, and the upper surface of the control unit 58 are flush.

As shown in FIG. 3, a depression is formed in the outer side surface of the left wall 14d, and a connector 64 is provided in the depression. A connector (not shown in the figure) provided at an electric wire such as a signal wire or a power wire connected to the sample is connected to the connector 64. An electric wire (signal wire, power wire) connected to the inner side of the connector 64 provided in the left wall 14d is also introduced into the control unit 58 through the space in the left wall 14d (this is not shown in the figure). Since the connector 64 is provided in the depression, the connector 64 does not hinder the operations performed by the operator. It is also possible not to provide the depression. When the connector is provided in the right wall 14e, the depression may be provided in the right wall 14e.

The tray 14 can be covered with the lid (cover) 68. As shown in FIGS. 1 and 2, the lid 68 serves to cover the accommodation portion 14c of the tray 14. The lid 68 is placed across the left wall 14d and the right wall 14e. In other words, the left and right side walls (left wall 14d and right wall 14e) function as support portions for supporting the left and right ends of the lid 68.

The lid 68 can be detachably attached to the tray 14. Pin support portions 69 for positioning are provided at the upper surface portions 14g of the left wall 14d and right wall 14e. The tray 14 can be positioned at a predetermined position by inserting the pins (not shown in the figure) provided at the lower surface in the corner portions of the lid 68 into the pin support portions 69. Where the lid 68 is pulled up so as to remove the pins from the pin support portions 69, the lid 68 can be taken off from the tray 14.

The lid 68 has an upper surface portion 68a and a leg portion 68b projecting in one direction (lower surface) from the left and right ends of the upper surface portion 68a. The rear end portion of the upper surface portion 68a is provided with an upper-surface notched portion 68c for forming a gap with the front surface of the control unit 58. The gap between the upper-surface notched portion 68c and the front surface of the control unit 58 has a width sufficient for a wiring to be passed therethrough. The upper-surface notched portion 68c may be also formed at the front end portion of the upper surface portion 68a so as to form a gap with the rear surface of the operation unit 56.

The leg portion 68b is provided with a side-surface notched portion 68d for forming a gap with the upper surface portion 14g of the side walls (left wall 14d and right wall 14e). The gap between the side-surface notched portion 68d and the upper surface portion 14g of the side walls (left wall 14d and right wall 14e) has a width sufficient for a wiring to be passed therethrough.

The lid 68 has a width same as the width of the operation unit 56 and the width (length in the left right direction) of the control unit 58. Therefore, where the lid 68 is placed on the tray 14 so as to bridge the two side walls (left wall 14d and right wall 14e) of the tray 14, the upper surface of the apparatus for environmental tests 10 assumes a flat substantially rectangular shape. Therefore, the personal computer 18 and the measuring instrument 16 can be placed on the upper surface.

The control unit 58 has a configuration in which a control substrate and the like are housed inside the case 58a, and a reinforcing member 71 (see FIG. 4) for increasing the rigidity of the case 58a is provided inside the case 58a so that the measuring instrument 16 and the like could be placed on the control unit 58. Thus, the reinforcing member 71 is mounted on the underside surface of the top plate 58b of the case 58a of the control unit 58. By fixedly attaching the reinforcing member 71 to the top plate 58b, it is possible to increase the rigidity of the top plate 58b. The reinforcing member 71 is not limited to the configuration that is attached to the underside surface of the top plate 58b. The reinforcing member 71 may be positioned in the central portion of the case 58a and may be placed on the upper surface of the top portion 28 of the chamber 12. In this case, the reinforcing member 71 supports the top plate 58b from below so as to prevent the central portion of the top plate 58b from sagging.

Figure 5:
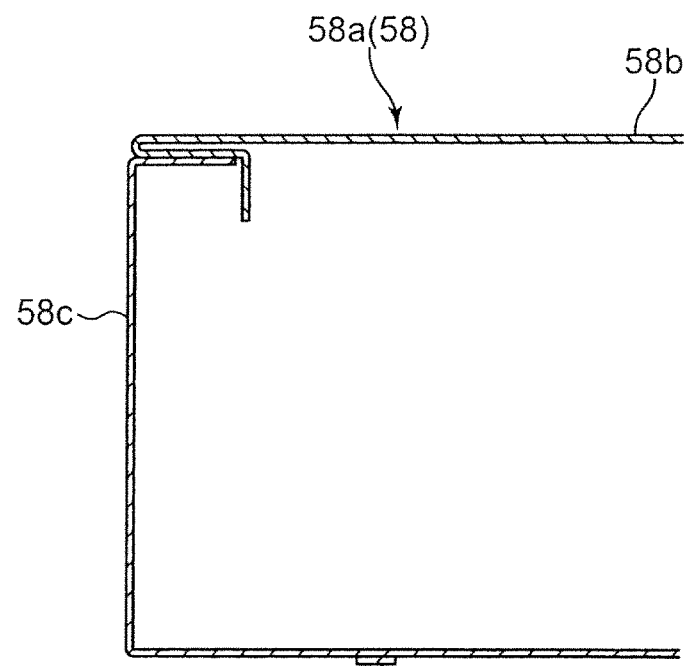
FIG. 5 is a cross-sectional view taken along the V-V line in FIG. 4.

Further, a configuration is used in which the rigidity of the case 58a is also increased on the circumferential edge of the case 58a. Thus, as shown in FIG. 5, the side plate 58c and the top plate 58b constituting the case 58a are formed from separate plate materials and the edges of the plate materials are joined together in a state of mutual overlapping. More specifically, the upper end portion of the plate material constituting the side plate 58c is bent horizontally. Meanwhile, the side end portion of the top plate 58b is bent back to obtain a double overlapping configuration. A triple overlapping structure is obtained by overlapping the upper end portion of the plate material constituting the side plate 58c and the side end portion of the plate material constituting the top plate 58b in the circumferential edge portion of the case 58a of the control unit 58. As a result, the rigidity is also increased in the circumferential edge portion of the case 58a, and the measuring instrument 16 and the like can be placed on the control unit 58.

The configuration is also used in which the rigidity of the left and right walls (left wall 14d and right wall 14e) of the tray 14 and the lid 68 is increased. Thus, as shown in FIG. 6, the side walls (left wall 14d and right wall 14e) of the tray 14 are configured by two plate materials, and the end portions of the two plate materials overlap in the upper surface portion 14g of the side walls (left wall 14d and right wall 14e). As a result, the rigidity of the side wall itself is increased. The side walls (left wall 14d and right wall 14e) of the tray 14 are not necessarily configured by two plate materials.

In the lid 68, the left and right ends of the plate material constituting the lid 68 are bent downward, and the bent sections are constituted as the leg portions 68b. The leg portion 68b is configured to include a vertical portion 68b1 projected downward from the upper surface portion 68a and a transverse portion 68b2 projected inward from the lower end portion of the vertical portion 68b1. The transverse portion 68b2 overlaps the upper surface portion 14g of the side walls (left wall 14d and right wall 14e). As a result, the rigidity of the lid 68 is increased and the measuring instrument 16 and the like can be also placed on the lid 68. The transverse portion 68b2 connected to the lower end of the vertical portion 68b1 projected downward is provided only in the vicinity of the pin and is not provided at the side-wall notched portion 68d. The leg portion 68b may be formed in a tubular shape of a rectangular cross section.

As explained hereinabove, in the present embodiment, the tray 14 is provided on the upper surface of the chamber 12. Therefore, for example, some of the wirings can be bundled and accommodated in the tray 14. Further, articles such as tools and materials relating to the test can be also accommodated therein. Therefore, the degradation of the environment surrounding the apparatus for environmental tests 10 can be inhibited.

Further, in the present embodiment, the front wall 14a of the tray 14 is constituted by the operation unit 56, and the rear wall 14b of the tray 14 is constituted by the control unit 58. Thus, since the front wall 14a and the rear wall 14b of the tray 14 are formed by using the operation unit 56 and the control unit 58, which are inherently necessary for the apparatus for environmental tests 10, the increase in the number of parts can be inhibited.

Further, in the present embodiment, the left and right side walls (left wall 14d and right wall 14e) of the tray 14 are configured by hollow bodies. Therefore, the wiring connecting the operation unit 56 and the control unit 58 can be allowed to pass inside the hollow bodies. As a result, even in the configuration in which the operation unit 56 and the control unit 58 are disposed at positions that are set apart from each other due to the formation of the tray 14, the wirings connecting the operation unit 56 and the control unit 58 can be prevented from being exposed.

Further, in the present embodiment, the lid 68 that can be attached to and detached from the tray 14 is provided. Therefore, in a state in which the lid 68 closes the upper surface of the tray 14, the articles accommodated inside the tray 14 are not visible from the outside. Therefore, the external appearance is improved. In a state in which the upper surface of the tray 14 is open, the articles such as wirings can be accommodated inside the tray 14.

Further, in the present embodiment, the notched portions 68c, 68d are formed in the lid 68. Therefore, wirings can be drawn from the outside into the tray 14 through a gap formed between the tray 14 and the notched portions 68c, 68d of the lid 68.

Further, in the present embodiment, the side walls (left wall 14d and right wall 14e) of the tray 14 function also as support portions that support the left and right ends of the lid 68. Therefore, the side walls (left wall 14d and right wall 14e) constituted by hollow bodies through which the wirings connecting the operation unit 56 and the control unit 58 can be allowed to pass can be also caused to function as the members ensuring the support rigidity of the lid 68.

Figure 17:
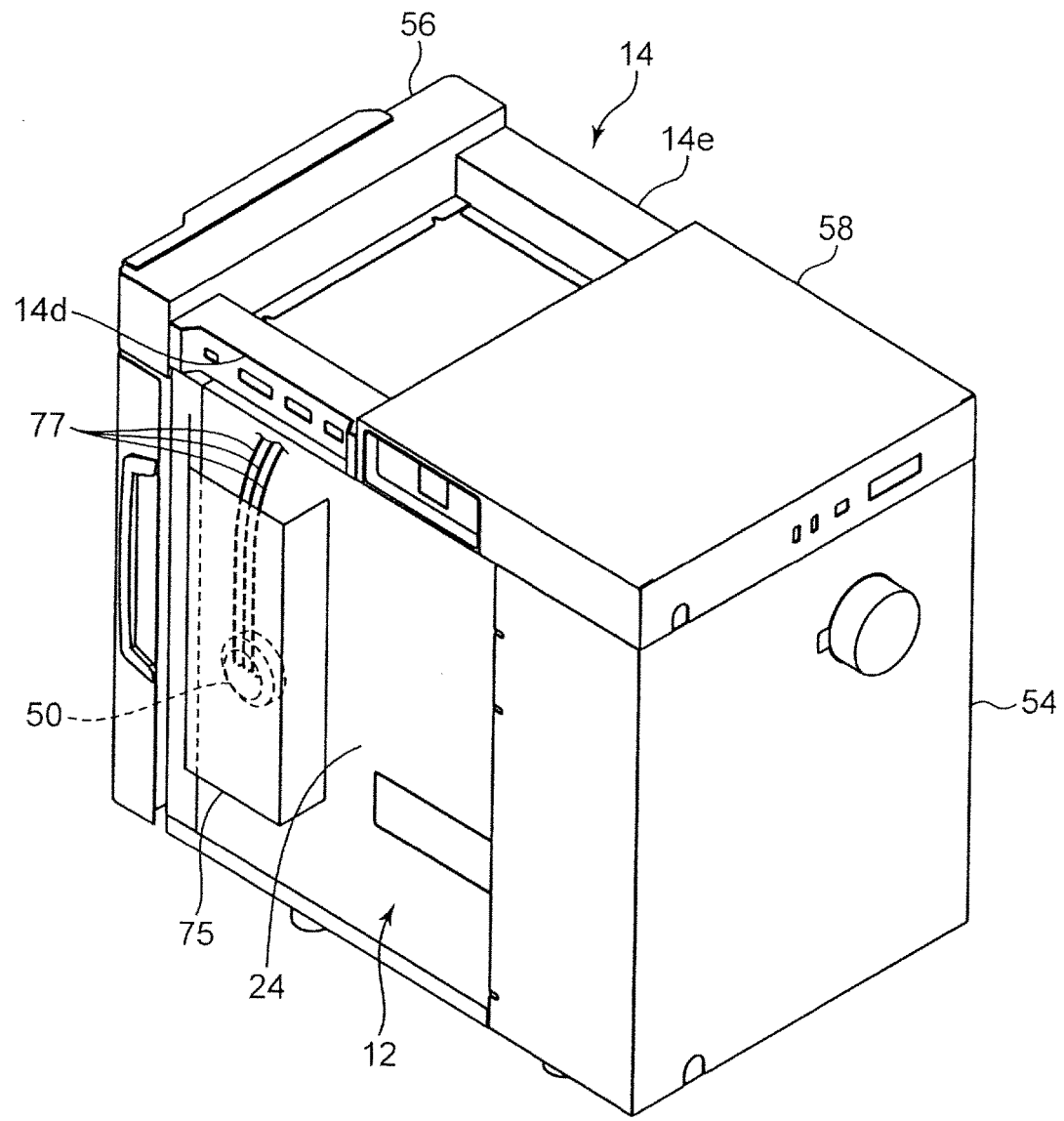
FIG. 17 illustrates the external appearance of the apparatus for environmental tests according to another embodiment of the present invention.

The present invention is not limited to the embodiments and can be variously changed and modified without departing from the essence of the invention. For example, as shown in FIG. 17, the apparatus for environmental tests 10 may be also provided with a side-surface duct 75. The side-surface duct 75 is configured to be attachable to the outer surface of the left wall 24 of the chamber 12 so as to cover the communication hole 50 formed in the left wall 24 of the chamber 12. Since a space is formed between the side-surface duct 75 and the outer surface of the left wall 24, the wiring 77 drawn out of the communication hole 50 can be drawn through this space to the upper side of the chamber 12. As a result, the degradation of the external appearance of the apparatus for environmental tests 10 can be inhibited. The communication hole 50 may be provided in the right wall 25. In this case, a side-surface duct 75 may be attached to the right wall 25.

Figure 18:
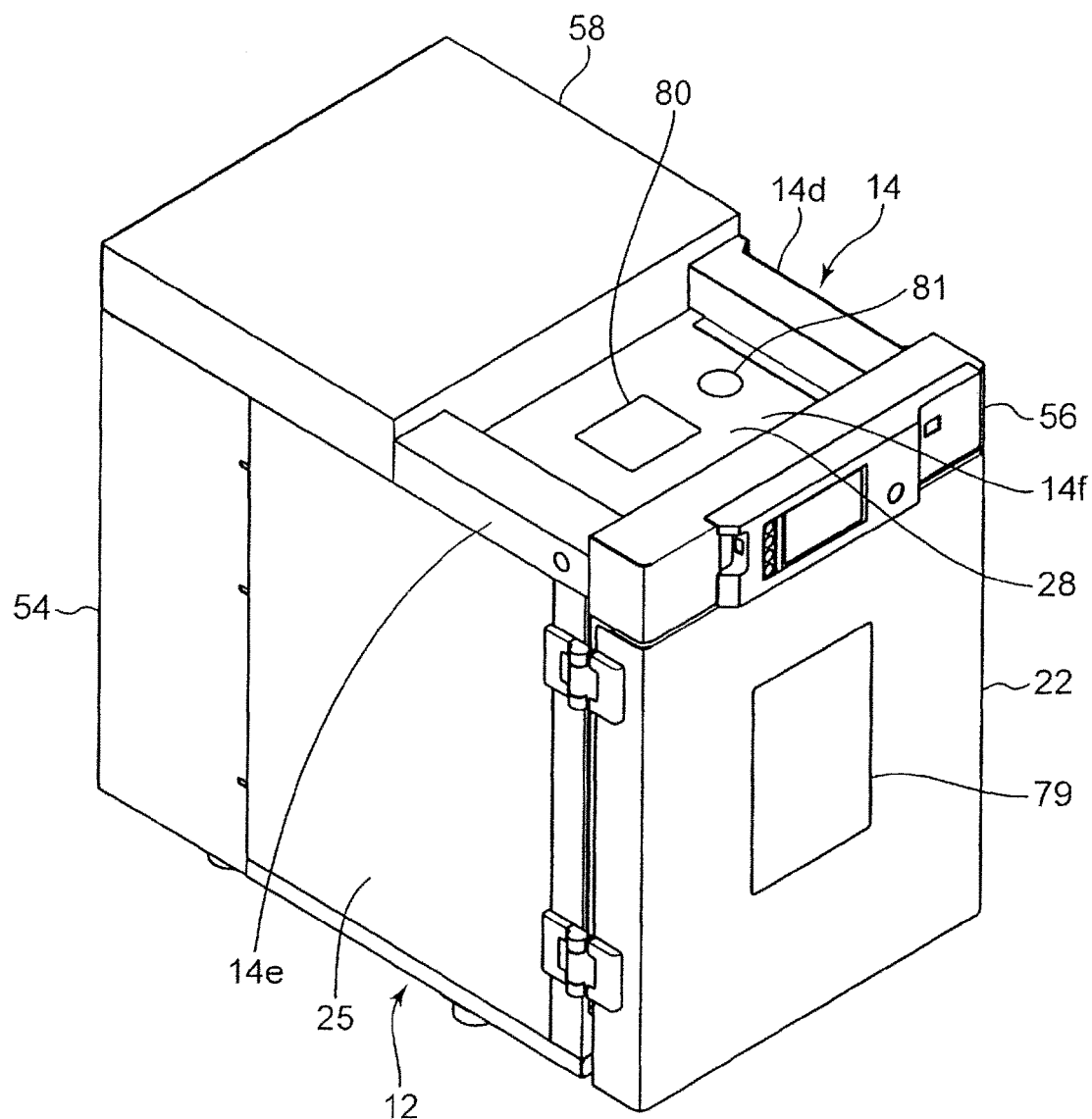
FIG. 18 illustrates the external appearance of the apparatus for environmental tests according to another embodiment of the present invention.

In the embodiment, the configuration is explained in which no observation window is formed in the door 22, but such a configuration is not limiting. As shown in FIG. 18, an observation window 79 enabling observation of the interior of the test space TS may be formed in the door 22. Further, an observation window 80 may be formed in addition to the observation window 79 or instead of the observation window 79 in the top portion 28 of the chamber 12. Further, a communication hole 81 for connecting the interior of the test space TS with the outside of the chamber 12 may be formed in the top portion 28 of the chamber 12. The observation window 80 and the communication hole 81 may be provided in a zone of the top portion 28 that functions as the bottom portion 14f of the tray 14. The observation windows 79, 80 are made, for example, from transparent sheets of glass or the like.

Figure 19:
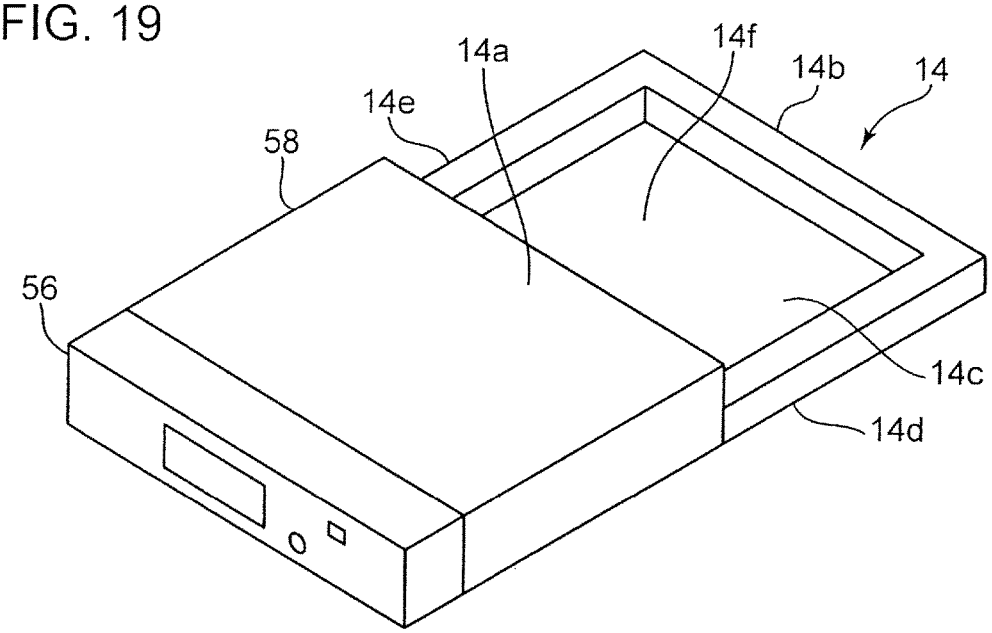
FIG. 19 shows the operation unit, control unit, and tray of the apparatus for environmental tests according to another embodiment of the present invention.

In the embodiment, a configuration is used, in which the operation unit 56 also functions as the front wall 14a of the tray 14, and the control unit 58 also functions as the rear wall 14b of the tray 14. Alternatively, a configuration may be also used in which the control unit 58 functions as the front wall 14a of the tray 14, as shown in FIG. 19. In this case, the operation unit 56 is disposed adjacently to the front side of the control unit 58 and, therefore, set apart from the accommodation portion 14c of the tray 14. In the tray 14, the rear wall 14b connecting the rear ends of the left wall 14d and right wall 14e is provided separately from the control unit 58.

Figure 20:
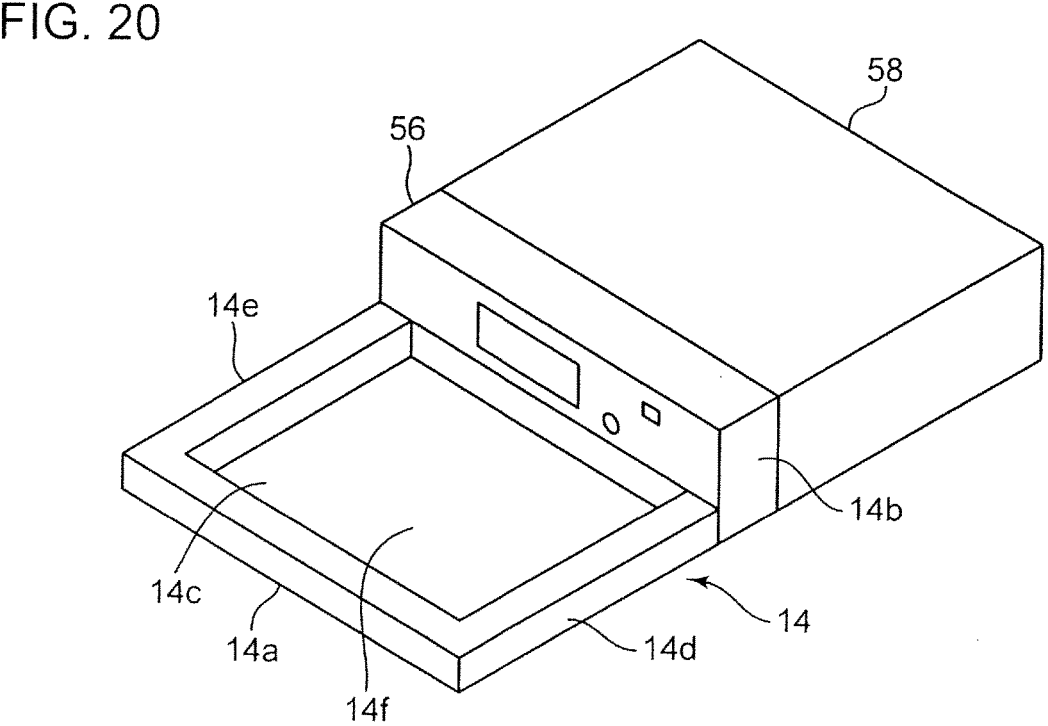
FIG. 20 shows the operation unit, control unit, and tray of the apparatus for environmental tests according to another embodiment of the present invention.

Further, as shown in FIG. 20, the operation unit 56 may be also configured to function as the rear wall 14b of the tray 14. In this case, the control unit 58 is disposed adjacently to the rear side of the operation unit 56 and, therefore, set apart from the accommodation portion 14c of the tray 14. In the tray 14, the front wall 14a connecting the front ends of the left wall 14d and right wall 14e is provided separately from the operation unit 56. In such a configuration, the operation unit 56 is at a distance from the opening that is opened and closed by the door 22. Therefore, the operation unit 56 is unlikely to be affected by the heat released from the test space TS when the door 22 is opened. Such a configuration can also use the lid 68. In this case, for example, the switches of the operation unit 56 are positioned on the upper side of the lid 68.

Figure 21:
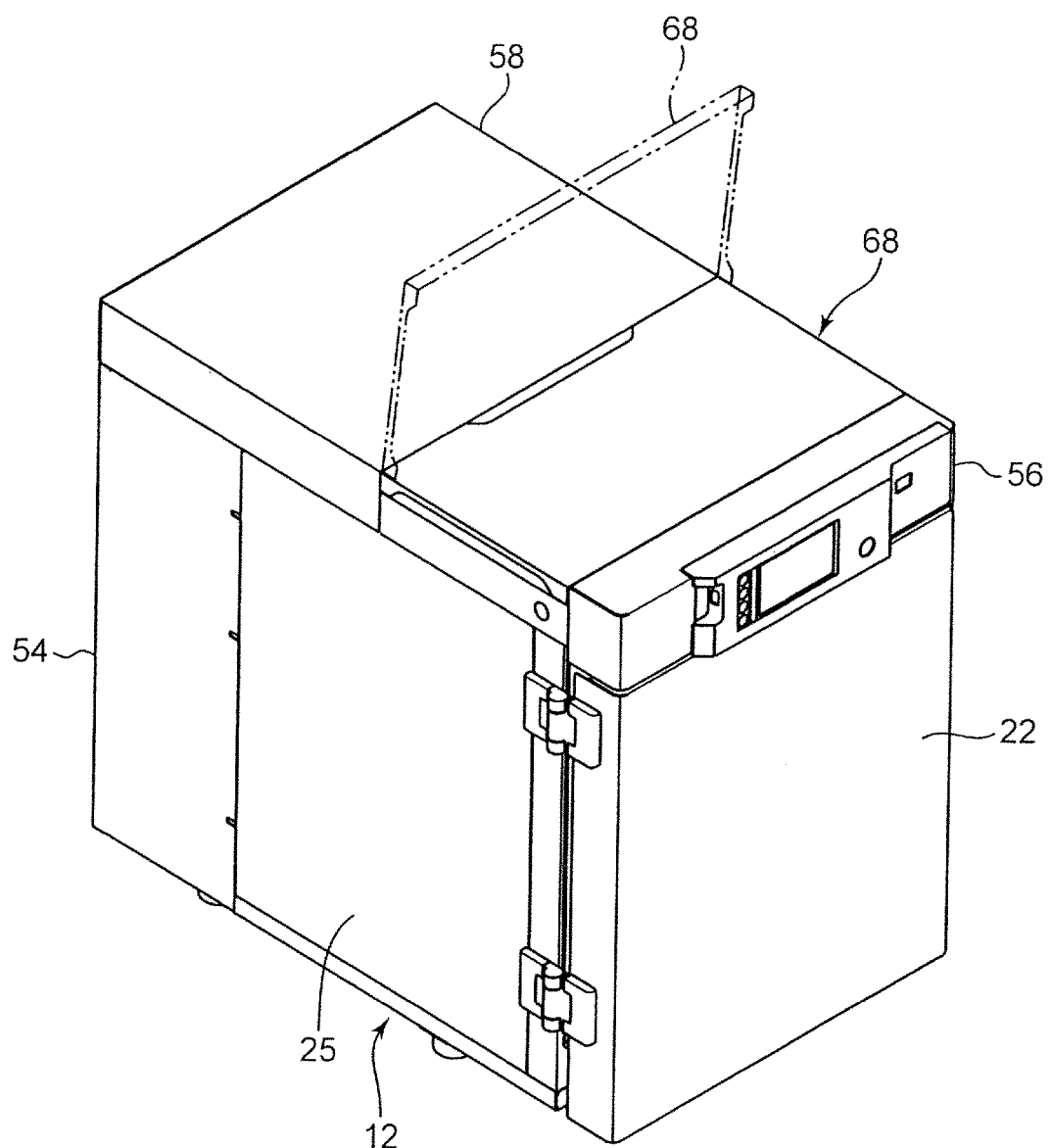
FIG. 21 shows the external appearance of the apparatus for environmental tests according to another embodiment of the present invention.

In the present embodiment, the lid 68 is configured to be detachably attached to the tray 14, but such a configuration is not limiting. As shown in FIG. 21, the lid 68 may be attached to the tray 14 so as to open and close the upper surface of the tray 14 by moving between a position in which the upper surface of the tray 14 is closed and a position in which the upper surface of the tray 14 is open. When the lid 68 is at the position in which the upper surface of the tray 14 is closed, the leg portion 68b of the lid 68 is placed on the side wall of the tray 14. Further, in the example illustrated by the figure, the configuration is shown in which the rear end portion of the lid 68 is rotatably supported by the tray 14, but any of the left end portion, right end portion, and front end portion of the lid 68 may be also rotatably supported by the tray.

In the embodiment the configuration provided with the lid 68 is shown, but such a configuration is not limiting. Thus, a configuration having no lid 68 may be also used. At least either of the upper-surface notched portion 68c and the side-surface notched portion 68d of the lid 68 may be omitted.

In the embodiment, the bottom portion 14f of the tray 14 is configured by the top portion 28 of the chamber 12, but such a configuration is not limiting. For example, the bottom portion 14f of the tray 14 may be configured by a member provided separately from the top portion 28.

Figure 22:
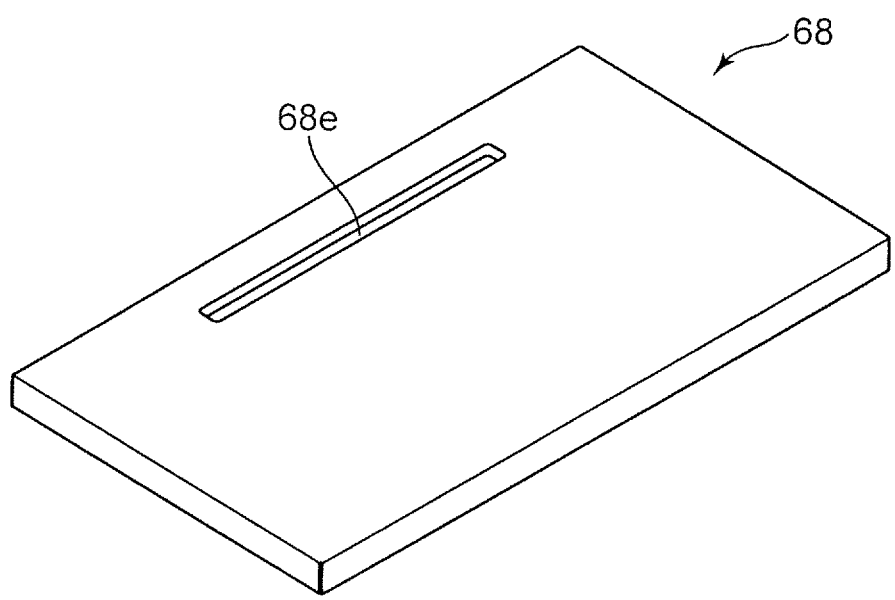
FIG. 22 shows a lid provided at the apparatus for environmental tests according to another embodiment of the present invention.

In the embodiment, the configuration is used in which the notched portions 68c, 68d are provided at the lid 68, but such a configuration is not limiting. Thus, a through hole (slit) 68e may be formed instead of the notched portions 68c, 68d (see FIG. 22) in the lid 68. In this case, the wiring can be drawn into the tray 14 from the outside through the through hole 68e.

In the embodiment, both the left wall 14d and the right wall 14e of the tray 14 are formed from hollow bodies, but such a configuration is not limiting. Thus, at least either of the left wall 14d and right wall 14e may be configured by a solid member (for example, a plate material or a rod-shaped member), rather than a hollow body. For example, in the configuration in which the operation unit 56 and the control unit 58 are arranged adjacently to each other, as shown in FIG. 19 or 20, it is not necessary to pass a wiring inside the left wall 14d and the right wall 14e. Therefore, both the left wall 14d and the right wall 14e may be formed from a solid member. In the configuration in which the operation unit 56 and the control unit 58 are set apart, both the left wall 14d and the right wall 14e can be configured by a solid member by adding a member through which the wiring can be passed or stretching the wiring along the side surface.

The embodiment is summarized below.

(1) In the embodiment, the tray is provided on the upper surface of the chamber. As a result, for example, partially bundled wirings can be accommodated in the tray, and the articles such as tools and materials relating to the test can be also accommodated therein. Therefore, the degradation of the environment surrounding the apparatus for environmental tests can be inhibited.

(2) Either of the front wall and rear wall of the tray may be configured by an operation unit where switches are provided or a control unit housing a control substrate. With such a configuration, either of the front wall and rear wall of the tray is formed using the operation unit or control unit which is an essential component of the apparatus for environmental tests. Therefore, the increase in the number of parts can be inhibited.

(3) The front wall of the tray may be configured by the operation unit, and the rear wall of the tray may be configured by the control unit. With such a configuration, the front wall and rear wall of the tray are formed using the operation unit or control unit which is an essential component of the apparatus for environmental tests. Therefore, the increase in the number of parts can be inhibited.

(4) The left and right walls of the tray may be configured by hollow bodies connecting the operation unit and the control unit. With such a configuration, the wiring connecting the operation unit and control unit can be passed inside the hollow bodies. Therefore by forming the tray, it is possible to prevent the exposure of the wiring connecting the operation unit and control unit even in the configuration in which the operation unit and the control unit are disposed apart from each other.

(5) A lid for covering the tray may be provided. In this case, the lid may be detachably attached to the tray or may be capable of opening and closing the upper surface of the tray. With such a configuration, when the lid closes the upper surface of the tray, the articles accommodated in the tray cannot be seen from the outside. Therefore, the external appearance is improved. Further, when the upper surface of the tray is open, the articles such as wirings can be accommodated in the tray or can be removed from the tray.

(6) The lid may be provided with a notched portion forming a gap with the tray, or a through hole. With such a configuration, a wiring can be drawn into the tray from the outside through a gap formed between the tray and the notched portion of the lid. Further, when the through hole is formed in the lid, the wiring can be drawn into the tray from the outside through the through hole.

(7) When the lid covering the tray is provided, the lid may be configured to be detachably attached to the tray or be capable of opening and closing the upper surface of the tray, and the hollow bodies may function as supports for supporting left and right end portions of the lid. With such a configuration, when the upper surface of the tray is closed with the lid, the articles accommodated in the tray cannot be seen from the outside. Therefore, the external appearance is improved. Further, when the upper surface of the tray is open, the articles such as wirings can be accommodated in the tray or removed from the tray. The hollow body through which the wiring connecting the operation unit and control unit can be passed can be caused to function as a member ensuring the support rigidity of the lid.

(8) A communication hole connecting the test space with the outside may be formed in a side wall of the chamber. In this case, a side-surface duct may be detachably provided to the outer surface of the side wall of the chamber so as to cover at least the communication hole. In such a configuration, the wiring drawn out of the communication hole can pass inside the side-surface duct. Therefore, the degradation of external appearance can be inhibited.

As mentioned hereinabove, according to the present embodiment, the degradation of the environment surrounding the apparatus for environmental tests can be inhibited.

This application is based on Japanese Patent application No. 2013-203524 filed in Japan Patent Office on Sep. 30, 2013, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. An apparatus for environmental tests comprising:
   a chamber having formed therein a test space for disposing a sample;
   a tray that is provided on an upper surface of the chamber, the tray having a front wall, a rear wall and an upper opening between the front wall and the rear wall;
   an operation unit bearing a switch; and
   a control unit having a control substrate,
   one of the operation unit and the control unit being part of the front wall of the tray, and the other of the operation unit and the control unit being part of the rear wall of the tray.

2. The apparatus for environmental tests according to claim 1, wherein
   the operation unit is part of the front wall of the tray, and the control unit is part of the rear wall of the tray.

3. The apparatus for environmental tests according to claim 2, wherein
   the tray further has a left wall and a right wall that further define the upper opening, the left wall and the right wall connecting the operation unit and the control unit, each of the left wall and the right wall defining a hollow body.

4. The apparatus for environmental tests according to claim 1, further comprising:
   a lid that covers the upper opening of the tray.

5. The apparatus for environmental tests according to claim 4, wherein
   the lid is provided with a notched portion forming a gap with the tray, or a through hole.

6. The apparatus for, environmental tests according to claim 4, wherein
   the tray further has a left wall and a right wall that further define the upper opening, the left wall and the right wall support left and right end portions of the lid, respectively.

7. The apparatus for environmental tests according to claim 1, wherein
   the chamber has a side wall formed with a communication hole connecting the test space with the outside, and the apparatus further comprising a side-surface member detachably attached to an outer surface of the side wall of the chamber to cover at least the communication hole.

8. The apparatus for environmental testing according to claim 4 wherein the lid is detachably attached to the tray.

9. The apparatus for environmental testing according to claim 4 wherein the lid is fixedly attached to the tray.

10. An apparatus for environmental tests comprising:
a chamber with a test space disposed in the chamber for disposing a sample;
a tray provided on an upper surface of the chamber and having an open upper surface; and
a lid that covering the tray, the lid being detachably attached to the tray or being configured to open and close the upper surface of the tray, the lid being provided with a notch that forms a gap with the tray, or being provided with a through hole.

\* \* \* \* \*